United States Patent
Vigdorchik et al.

(10) Patent No.: US 11,544,850 B1
(45) Date of Patent: Jan. 3, 2023

(54) SYSTEM AND METHOD FOR PATIENT-SPECIFIC ANATOMICAL ANALYSES

(71) Applicant: Ortho AI LLC, New York, NY (US)

(72) Inventors: Jonathan Vigdorchik, Brooklyn, NY (US); Seth Jerabek, Pelham, NY (US); David Mayman, New York, NY (US)

(73) Assignee: Ortho AI LLC, New York, NY (US)

( * ) Notice: Subject to any disclaimer, the term of this patent is extended or adjusted under 35 U.S.C. 154(b) by 0 days.

(21) Appl. No.: 17/738,163

(22) Filed: May 6, 2022

(51) Int. Cl.
| | |
|---|---|
| *G06K 9/00* | (2022.01) |
| *G06T 7/00* | (2017.01) |
| *A61B 5/00* | (2006.01) |
| *A61B 5/11* | (2006.01) |
| *G06T 7/11* | (2017.01) |
| *G06T 7/73* | (2017.01) |
| *G06T 7/60* | (2017.01) |

(52) U.S. Cl.
CPC .......... *G06T 7/0012* (2013.01); *A61B 5/1121* (2013.01); *A61B 5/4566* (2013.01); *A61B 5/4571* (2013.01); *A61B 5/742* (2013.01); *G06T 7/11* (2017.01); *G06T 7/60* (2013.01); *G06T 7/73* (2017.01); *G06T 2207/30012* (2013.01)

(58) Field of Classification Search
CPC .................................................. G06T 7/0012
See application file for complete search history.

(56) References Cited

U.S. PATENT DOCUMENTS

| | | | | |
|---|---|---|---|---|
| 10,777,315 | B2 * | 9/2020 | Zehavi | G06T 7/70 |
| 2022/0000556 | A1 * | 1/2022 | Casey | G16H 50/30 |
| 2022/0254018 | A1 * | 8/2022 | Zhang | A61B 5/7267 |

FOREIGN PATENT DOCUMENTS

| | | | | |
|---|---|---|---|---|
| FR | 3106972 A1 * | 8/2021 | ............ | A61B 34/10 |
| WO | WO-0211633 A2 * | 2/2002 | ............ | A61B 17/02 |

OTHER PUBLICATIONS

Gomez et al., Precision and accuracy of pre-surgical planning of non-cemented total hip replacement with calibrated digital images and acetates, Journal of Orthopaedic Surgery and Research (2021), pp. 1-6.

Krueger et al., Substantial Preoperative Work is Unaccounted for in Total Hip and Knee Arthroplasty, The Journal of Arthroplasty 35, 2020, pp. 2318-2322.

Meermans et al., Preoperative Radiographic Assessment of Limb-length Discrepancy in Total Hip Arthroplasty, Clin Orthop Relat Res (2011) 469:1677-1682.

(Continued)

*Primary Examiner* — Oneal R Mistry

(74) *Attorney, Agent, or Firm* — Nicholas Pfeifer; Smith & Hopen, P.A.

(57) ABSTRACT

A system and method for determining patient-specific anatomical parameters to improve surgical outcomes. Some embodiments include processes for predicting the parameters of occluded anatomy. Some embodiment includes processes for more accurately identifying a center point of a ball and socket joint, such as a center point or center of rotation of a femoral head. Some embodiments include processes for identify a patient-specific spinal curvature, including more precisely determining patient specific spinal inflection points. The various steps can be performed automatically through trained computing devices and graphically presented to a surgeon for review and any necessary modifications.

20 Claims, 21 Drawing Sheets

(56) References Cited

OTHER PUBLICATIONS

Ronneberger et al., U-Net: Convolutional Networks for Biomedical Image Segmentation, Computer Science Department and BIOSS Centre for Biological Signalling Studies, University of Freiburg, Germany, May 2015.

Rouzrokh et al., A Deep Learning Tool for Automated Radiographic Measurement of Acetabular Component Inclination and Version After Total Hip Arthroplasty, The Journal of Arthroplasty 36, 2021, pp. 2510-2517.

Schwartz et al., Deep Learning Automates Measurement of Spinopelvic Parameters on Lateral Lumbar Radiographs, SPINE vol. 46, No. 12, pp. E671-E678.

Tack et al., Fully automated Assessment of Knee Alignment from Full-Leg X-Rays employing a "YOLOv4 and Resnet Landmark regression Algorithm" (YARLA): Data from the Osteoarthritis Initiative, Computer methods and programs in Biomedicine 205, 2021, 106080.

Tipton et al., The Assessment of Limb Length Discrepancy Before Total Hip Arthroplasty, The Journal of Arthroplasty 31 ,2016, pp. 888-892.

Yang et al., Feasibility of automatic measurements of hip joints based on pelvic radiography and a deep learning algorithm, European Journal of Radiology 132, 2020, 109303.

\* cited by examiner

Plot Anterior Spinal Points

Plot Posterior Spinal Points

103

Complete Spine

SYSTEM AND METHOD FOR PATIENT-SPECIFIC ANATOMICAL ANALYSES

BACKGROUND OF THE INVENTION

1. Field of the Invention

This invention relates, generally, to orthopedics. More specifically, it relates to patient-specific anatomical analyses and surgical planning.

2. Brief Description of the Prior Art

Traditional approaches to surgery often fail to account for various patient-specific anatomical features that can have a significant impact on the outcome of the procedure. In considering hip replacement surgery (also called "total hip arthroplasty") as an example, the traditional approach is to focus primarily on the patient's hip joint. However, the patient's hip joint is just a portion of the patient's moveable pelvis, which is connected to the patient's mobile spine. These moving parts are all interconnected and can have a significant impact on the hip joint.

More specifically, the patient's pelvis will inherently change position/orientation when the patient is in different positions (e.g., the standing, laying, and seated positions). The same is true of the patient's spine. The curvature and mobility of the patient's spine can further alter the patient's pelvic orientation/position in the various positions in which a patient moves. The combined anatomical features and movements of the spine and pelvis will impact the type, size, shape, and location of the prostheses used to replace the patient's hip. Thus, it is important for a surgeon to consider not only the state of the hip joint and femoral head, but also the pelvic position and mobility along with the spinal curvature and mobility.

In addition, poor image quality and/or anatomical deformities can make it difficult to impossible for a surgeon to accurately identify various anatomical features and landmarks of a patient. For example, it can be difficult to impossible to accurately identify the center point of the patient's femoral head and/or point of rotation of the hip joint. Even a minor error in determining the point of rotation of the hip joint can have a drastic impact on the surgical approach and the end result of the surgery.

As another example, consider the spine. Typical lateral imaging often results in anatomical obstructions occluding certain vertebra in the lateral image. Commonly, a lateral medical image produces occluded thoracic vertebrae. There is simply too much bony anatomy obstructing the view of the thoracic vertebrae when viewed from a lateral position. Similarly, medical imaging could produce poor results making it difficult to impossible for the surgeon to identify the anatomical characteristics of other vertebrae in the spine.

For these reasons, the typical approach to surgery, such as hip replacement surgery, often fail to consider the characteristics of the spine and fail to accurately and consistently identify various anatomical landmarks. In an attempt to overcome these issues, some surgeons will use the lordosis and kyphosis angle to assess spinal curvature. These values are measured using historic vertebrae landmarks such as the L1 vertebral edge and sacral top plate. These landmarks are used because they are easily reproducible and measurable on typical medical images. However, this approach does not capture the full curvature of the hip and spine because the patient's anatomical hip characteristics (i.e., inferior to the sacrum) are often ignored. Furthermore, one person's L1 might not be at the same place of spinal curvature as another person's L1. Thus, using these historic landmarks is not the best approach to fully assess an individual's anatomy. In contrast, determining the exact inflection points of the spine (including the sacrum) would provide a more quantitative analysis of a patient's individual spinal morphology resulting in improved surgical outcomes.

Accordingly, what is needed is a system and method to more accurately and more thoroughly identify and assess a patient's unique anatomy. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a system and method to more accurately and more thoroughly identify and assess a patient's unique anatomy from a medical image is now met by a new, useful, and nonobvious invention.

Some embodiments of the present invention include one or more computers configured to perform the steps described herein to determine patient-specific anatomical parameters. Some embodiments include a method for determining patient-specific anatomical parameters. The steps include first acquiring digital medical images of a patient. From the medical images, the anatomy of interest is identified. In some embodiments, the anatomy of interest includes at least a portion of a spine. In some embodiments, the anatomy of interest further includes at least one femoral head and at least a portion of a sacrum.

Some embodiments further include segmenting the anatomy of interest to create a digital representative image of the anatomy of interest separate from the acquired medical image. In the representative image, a series of anatomical landmarks are identified on the anatomy of interest. In some embodiments, the anatomical landmarks include at least one anterior and/or posterior vertebral point on a superior and/or inferior edge of one or more vertebrae. In some embodiments, the anatomical landmarks further include a center point of the at least one femoral head and a sacral end plate.

A best fit line of the spine can then be calculated based on a best fit line of the spine. Based on the best fit line, patient-specific spinal inflection points are determined. In some embodiments, the spinal inflection points are based on calculating a derivative of an equation representing the best fit line of the curvature of the spine.

Some embodiments further include quantitatively determining patient-specific spinopelvic parameters based on at least one of the center point of the at least one femoral head, a sacral slop, and the patient-specific inflection points of the spine. The spinopelvic parameters may include a pelvic tilt, a pelvic incidence, a sacral slope angle, one or more Cobb angles, a lordosis angle, and/or a kyphosis angle. The results can be displayed on a graphic user interface.

Some embodiments further include determining if the anatomy of interest includes occluded vertebrae. In some embodiments, the spine is separated into two or more segments in response to the anatomy of interest including occluded vertebrae. In response to a determination that the anatomy of interest includes occluded vertebrae, a best fit line of a curvature of the spine is calculated; an average anterior-posterior (AP) width of at least some vertebrae is calculated; an anterior best fit line and a posterior best fit line is calculated; an anterior point and a posterior point on both the superior edge and the inferior edge of the at least some vertebrae is identified; a location of the occluded vertebrae is calculated with respect to an immediately adjacent vertebrae based on a spacing between the anterior points and the posterior points of the immediately adjacent vertebrae; and then a digital representation of the occluded vertebrae is inserted into the representative image. In some embodiments, the anterior best fit line is spaced from the posterior best fit line a distance generally equal to or less than the calculated average AP width of the vertebrae.

In some embodiments, the step of identifying the center point of the at least one femoral head includes placing two or more pairs of points along a perimeter boundary of the at least one femoral head; identifying a midpoint between a line extending between each pair of points; extending a perpendicular line from each midpoint and identifying a point of intersection or an average point of intersection amongst the perpendicular lines; and identifying the point of intersection or the average point of intersection as the center point.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which.

DETAILED DESCRIPTION OF THE INVENTION

Figure 1:
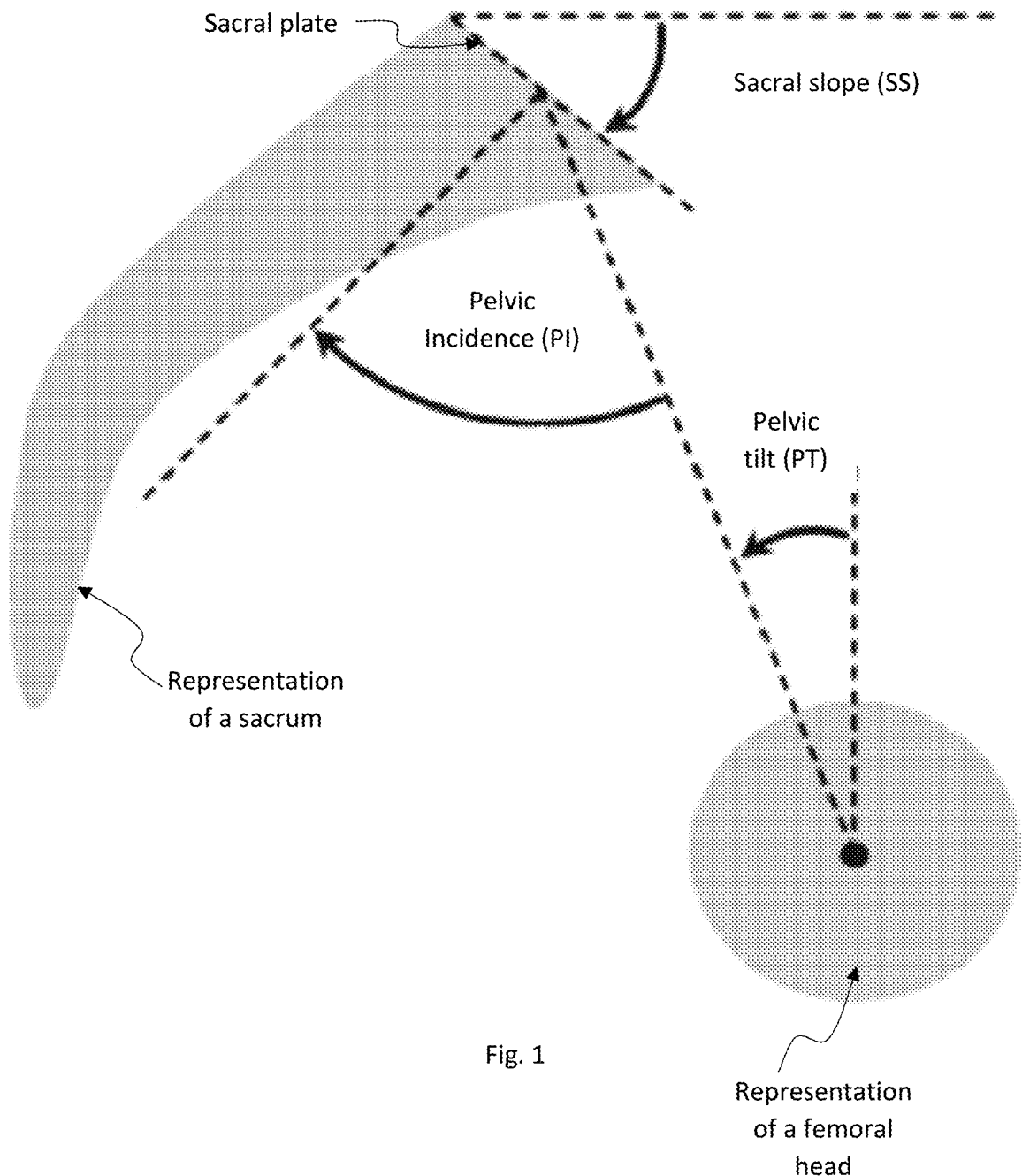
FIG. 1 is a representative diagram illustrating the relationship between the pelvic tilt, sacral slope, and pelvic incidence.

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

In the following description, for the purposes of explanation, numerous specific details are set forth in order to provide a thorough understanding of embodiments of the present technology. It will be apparent, however, to one skilled in the art that embodiments of the present technology may be practiced without some of these specific details. The techniques introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions which may be used to program a computer (or other electronic devices) to perform a process. The machine-readable medium may include, but is not limited to, floppy diskettes, optical disks, compacts disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions.

The phrases "in some embodiments," "according to some embodiments," "in the embodiments shown," "in other embodiments," and the like generally mean the particular feature, structure, or characteristic following the phrase is included in at least one implementation. In addition, such phrases do not necessarily refer to the same embodiments or different embodiments.

As used herein, the term "medical images" refers to images depicting a patient's anatomy, including but not limited to radiographic and x-ray images. Alternative types of medical images known to a person of ordinary skill in the art may be used. The present invention may be adapted to receive the image files in any format including, but not limited to .png, .bmp, .jpg, and DICOM format. Some embodiments of the present invention include imaging devices configured to capture the medical images of the patient. Alternatively, the system is configured to access one or more databases to retrieve the required medical images.

As used herein, the term "lateral image" refers to an image taken from a lateral side of the patient. A person of ordinary skill in the art will understand that a perfectly lateral view can be difficult to capture and that minor angular offsets from a perfectly lateral image are still useable with the present invention as will be explained in greater detail below.

As used herein, the term "pelvic tilt" refers to the forward or backward rotation/leaning of the pelvis. An example of pelvic tilt is depicted in FIG. 1.

As used herein, "sacral slope" refers to the angle between the horizontal axis and the sacral endplate. In some embodiments, the sacral slope can be determined by relying on other vertebral anatomical landmark, however, different vertebral anatomical landmark will alter the constants and the pelvic incidence. To ensure accuracy, the same vertebral anatomical landmark should be used throughout the preoperative and intraoperative analyses.

As used herein, the "spinopelvic tilt angle" ("SPT angle") is a reference of the amount of forward or backward lean of the pelvis, as shown in a lateral image. The SPT angle can be calculated as the angle between a line running from the vertebral anatomical landmark midpoint to the center of the femoral head and the vertical axis. In some embodiments, the SPT angle is calculated as the angle between a line running from the sacral endplate midpoint to the center of the femoral head and the vertical axis.

As used herein, "pelvic incidence" refers to the angle between a line perpendicular to the sacral plate at its midpoint and a line connecting this point to the femoral head axis. Pelvic incidence establishes a relationship between the pelvic tilt and the sacral slope. The tilt and the slope are inversely reciprocal. More specifically, the pelvic incidence angle equals the sum of the sacral slope angle and the SPT angle.

Referring now to the specifics of the present invention, some embodiments, include one or more computer systems having a memory, a user interface with a visual display (also referred to as a "graphic user interface" or "GUI"), and a processor for executing a program performing at least the steps described herein. In some embodiments, the present invention is a computer executable method or is a method embodied in software for executing the steps described herein. Further explanation of the hardware and software can be found in the Hardware and software infrastructure examples section below.

The present invention includes a system and method configured to better identify patient-specific anatomical landmarks and measure anatomical parameters and features. In some embodiments, the system and method further include using said landmarks and measurement to establish a surgical plan, identify proper protheses, and/or execute surgery.

In some embodiments, the present invention includes machine learning technology (referred to herein after as "a ML machine"). Such embodiments include one or more trained ML machines. The ML machine is first trained or is acquired as a pre-trained machine. During training, the ML machine is fed medical images and attempts to identify anatomy of interest (AOI) and/or anatomical landmarks on the medical images. In some embodiments, the ML machine is further trained and configured to perform the various additional steps described herein.

While some embodiments of the present invention use a computer system, such as an ML machine to automatically perform one or more of the various steps described herein, some embodiments may include user action. For example, the various steps described herein may be reviewed by a user for accuracy. In addition, the results following the various steps described may be visually displayed on a GUI to provide the user with the ability to review and, in some embodiments, modify the results. Thus, the user is also provided with controls to remove, change, or add in AOI, landmarks, features, measurements, etc.

In some embodiments, the system displays to a user the results after one or more steps in each of the different processes described herein. In some embodiments, the system displays to a user the results after every step in each of the different processes described herein.

Figure 2:
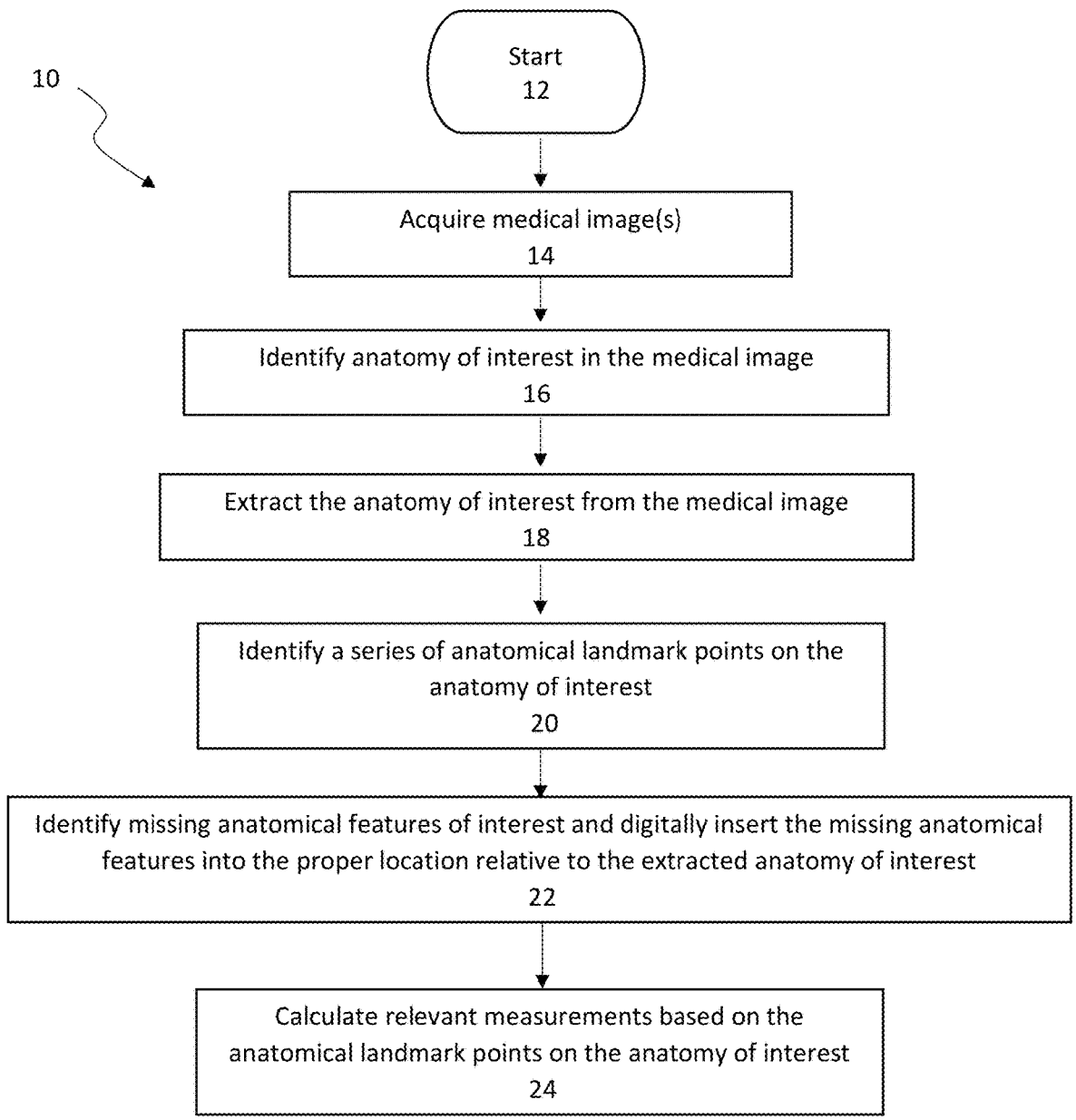
FIG. 2 is a flowchart of an embodiment of the present invention.

FIG. 2 provides a broad overview of the workflow of an embodiment of present invention generally denoted by reference numeral 10. The system or method is initiated at step 12 and one or more medical images of the patient's anatomy are acquired at step 14. At step 16 the system or a user identifies anatomy of interest ("AOI") from the medical images. Some embodiments of the present invention extract the AOI from the original medical image to provide an image of the AOI segmented (also referred to herein as a "digital representation" of the AOI) from the medical image at step 18. The system then identifies a series of anatomical landmark points on the AOI in step 20. Some embodiments further include identifying missing AOI and digitally inserting the missing AOI or anatomical features into the proper location relative to the extracted AOI in step 22. At step 24, the system calculates relevant measurements based on the anatomical landmark points. In some embodiments, the system then displays the results on a user interface. Upon satisfactory results, the system or the user can use the calculated measurements to select the preferred prosthesis, establish a surgical plan, and/or perform surgery.

For the sake of brevity and clarity, this disclosure will focus on hip replacement/revision surgery and also spinal surgery. Thus, the exemplary AOI hereinafter corresponds to the patient's spine, pelvis, and at least one femoral head. However, a person of ordinary skill in the art will understand that some aspects of the present invention can be used for other types of surgeries.

Figure 3:
FIG. 3 is an exemplary lateral medical image taken from Yitong Pan, Lateral Full-Spine X-Ray Image Dataset, copyrighted and subject to Creative Commons Attribution License (https://creativecommons.org/licenses/by/4.0/), available at: https://ieee-dataport.org/documents/lateral-full-spine-x-ray-image-dataset.

As previously mentioned, the present invention captures or acquires one or more medical images of a patient, such as exemplary image 102 in FIG. 3. In some embodiments, the medical images include a lateral image. Preferably the medical images capture a portion of the patient's AOI. With respect to hip surgery, the AOI often includes the patient's vertebrae 105, sacral plate 107, femoral heads 109, pubic symphysis, and ischial wings. The image may be acquired from an imaging machine, may be transferred to the one or more computer systems of the present invention, or may be retrieved from a datastore via a computer network. Alternatively, the images may be acquired through other methods known to a personal of ordinary skill in the art.

Once the medical image(s) 102 are acquired, the AOI are identified in the medical images. In some embodiments, the AOI's are identified by highlighting the individual anatomical structures in the medical image 102 as exemplified in FIG. 4. Preferably, the individual anatomical structures are identified in a way so that they standout in comparison to the surrounding anatomy depicted in medical image 102. However, any approach can be used to identify the individual anatomical structures in medical image 102.

Figure 4:
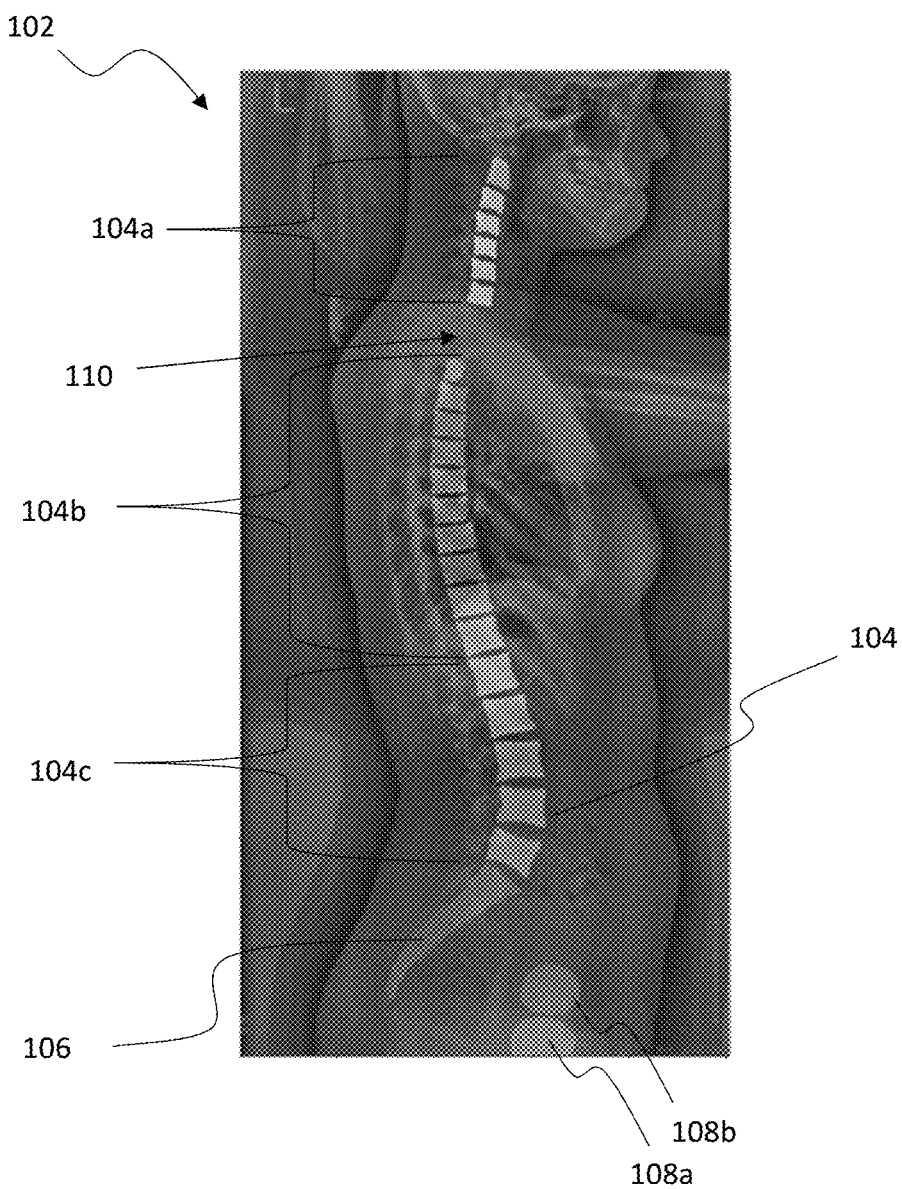
FIG. 4 is a digitally modified version of FIG. 3 illustrating an embodiment of the present invention in which AOI is highlighted on a medical image.

As exemplified in FIG. 4, some anatomical structures of the AOI are not identifiable in the medical image. The non-visible/non-identifiable AOI is sometimes referred to herein as "occluded" AOI. Occluded AOI can occur for various reasons, including but not limited to poor image quality or other anatomical structures residing between the imaging device and the AOI, such that the AOI is indistinguishable from the other anatomical structures.

FIG. 4 depicts occluded vertebrae 110 between cervical vertebrae 104*a* and thoracic vertebrae 104*b* of the spine. It should be understood however that various other anatomical structures of the AOI could be occluded. For example, one or more of the lumbar vertebrae 104*c* or portions of the sacral plate 106 may not be visible. Depending on which anatomical structures are occluded, the present invention may ignore the occluded anatomical structures or may perform a series of steps to digitally derive the occluded anatomical structures. These steps will be discussed in greater detail below.

Figure 5:
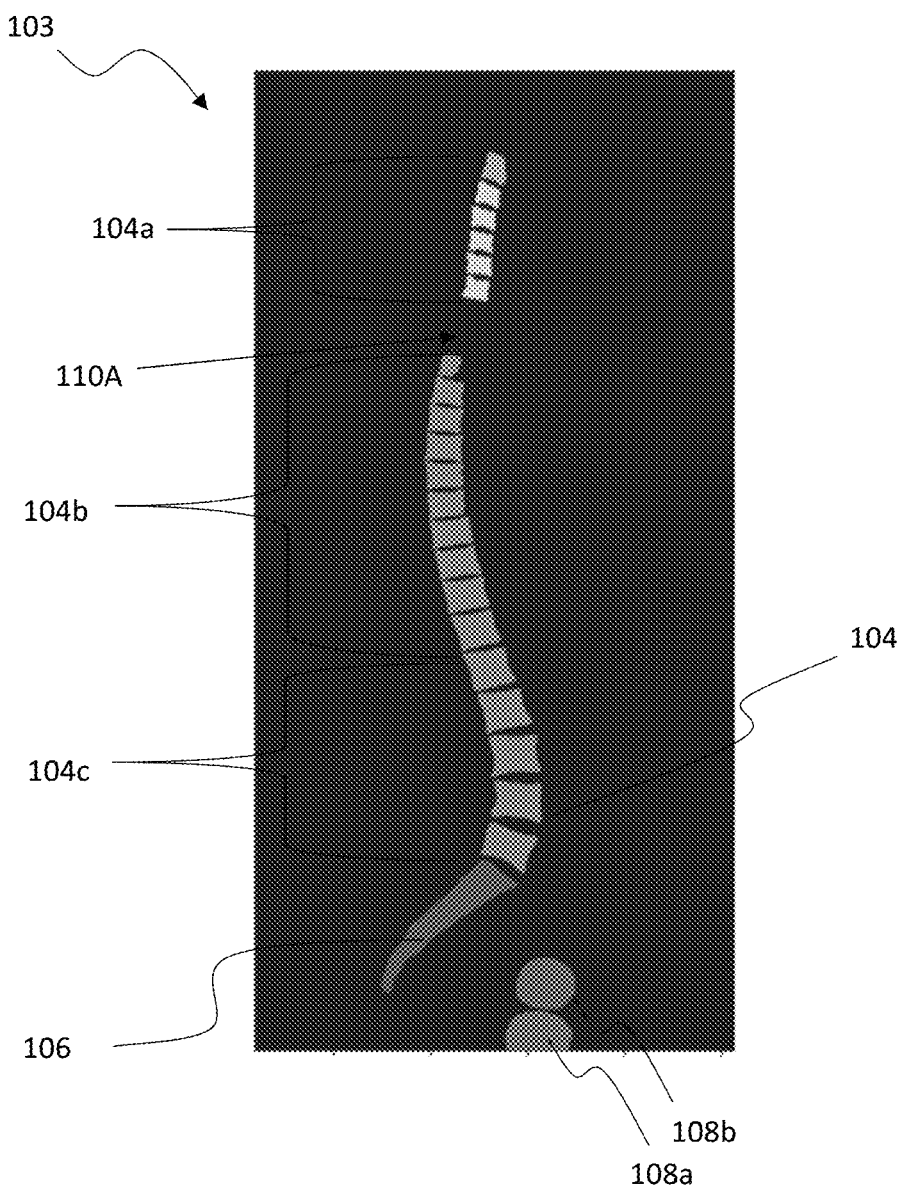
FIG. 5 is an embodiment of a representative image of the patient's AOI as identified in a medical image.

Referring now to FIG. 5, some embodiments of the present invention include extracting the identified AOI from medical image 102. The extracted AOI can then be displayed to the user as segmented image 103 in an effort to improve clarity and eliminate the unnecessary information from view. At this point, the system can again provide segmented image 103 to the user for review and approval. The user is also provided with controls to remove, change, or add in AOI identifications in segmented image 103 or in medical image 102 with the identified AOI highlighted.

Figure 6:
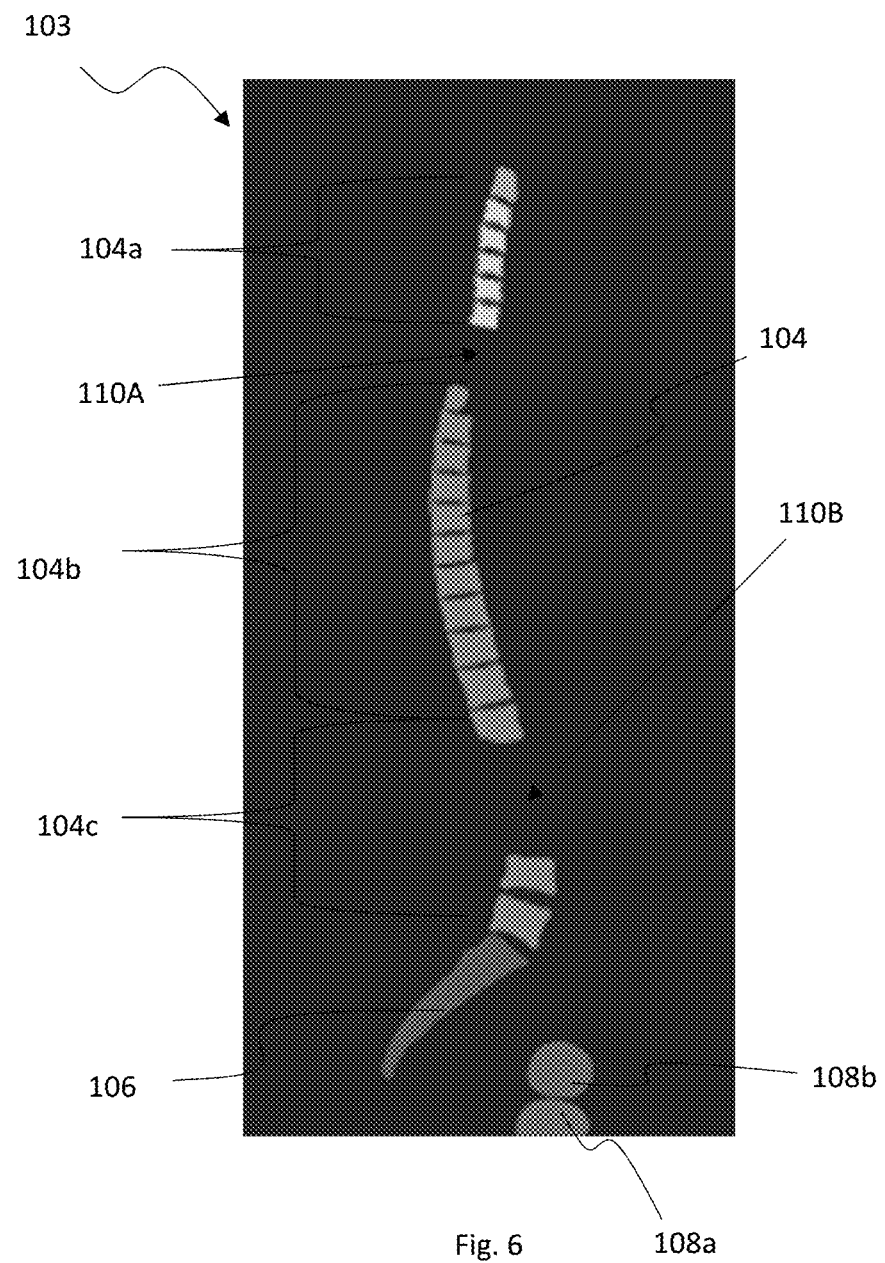
FIG. 6 is an embodiment of a representative image of the patient's AOI as identified in a medical image.

FIG. 6 provides another example of segmented image 103 of extracted AOI. However, this example stems from a medical image (not exemplified in a figure) that has occluded vertebrae 110A in the cervical/thoracic region and occluded vertebrae 110B in the lumbar section of the patient's spine. With more vertebrae missing, it becomes increasingly difficult to determine the curvature of the spine and determine various anatomical measurements and angles necessary for surgical planning, prostheses selection, and/or execution of surgery.

Once the AOI is identified, and extracted in some embodiments, a plurality of landmarks points is identified. The landmarks are identified via a user, automatically using a trained ML machine, or through another system or method known in the art. Furthermore, while the landmarks disclosed herein are particularly necessary for certain hip surgery and/or spinal surgery, it should be understood that different landmarks can be used depending on the surgery, the surgeon's preferences, or the patient's anatomy.

In some embodiments, a series of anatomical landmarks are visually identified in the representative image of the extracted AOI. Because the exemplary embodiment described herein is focused on the hip and spine, the exemplary series of anatomical landmarks on which this section focuses includes hip landmarks and spinal landmarks, each of which will be discussed below.

The series of hip landmarks include but is not limited to the center of the femoral head(s) or center of rotation of the femoral head(s), the sacral plate edge (also referred to as the "sacral endplate" or "top plate"), the pubic symphysis, and the iliac wings. In some embodiments, each landmark is identified in medical image 102 and/or segmented image 103 in accordance with known techniques. While the landmarks may be identified and displayed on medical image 102, hereinafter the disclosure will refer to an embodiment in which the landmarks are identified and displayed on segmented image 103 for the sake of brevity and clarity.

It should also be noted that some embodiments need not display the identified landmarks on the images in order to calculate various measurements. However, displaying the identified landmarks on the images is useful for quality control and visual verification by the user. In addition, displaying the identified landmarks on the image is useful when the embodiment also includes an option for a user to modify the location or other characteristics of the identified landmarks.

Figure 7:
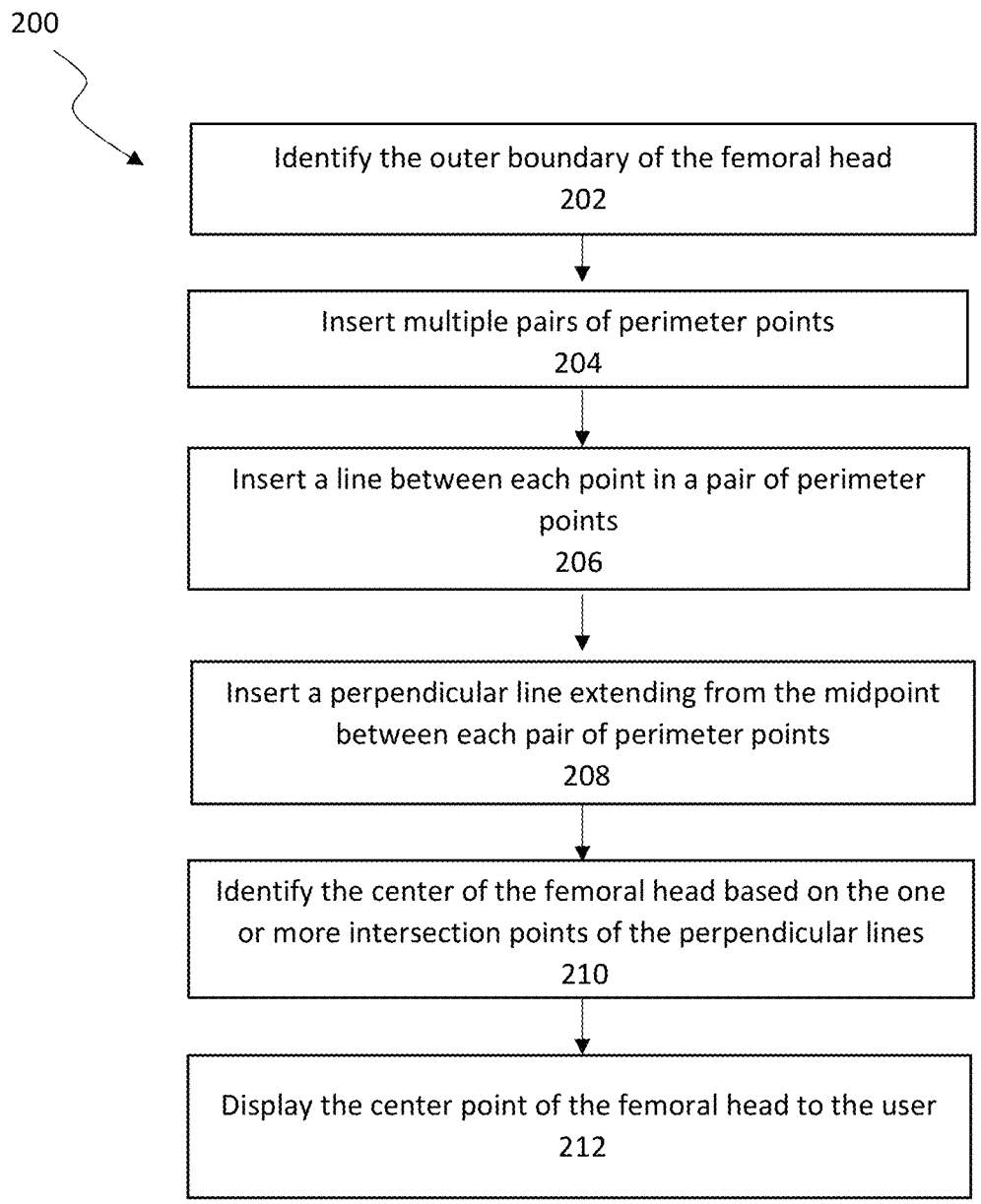
FIG. 7 is a flowchart of an embodiment of one of the processes of the present invention.
Figure 8:
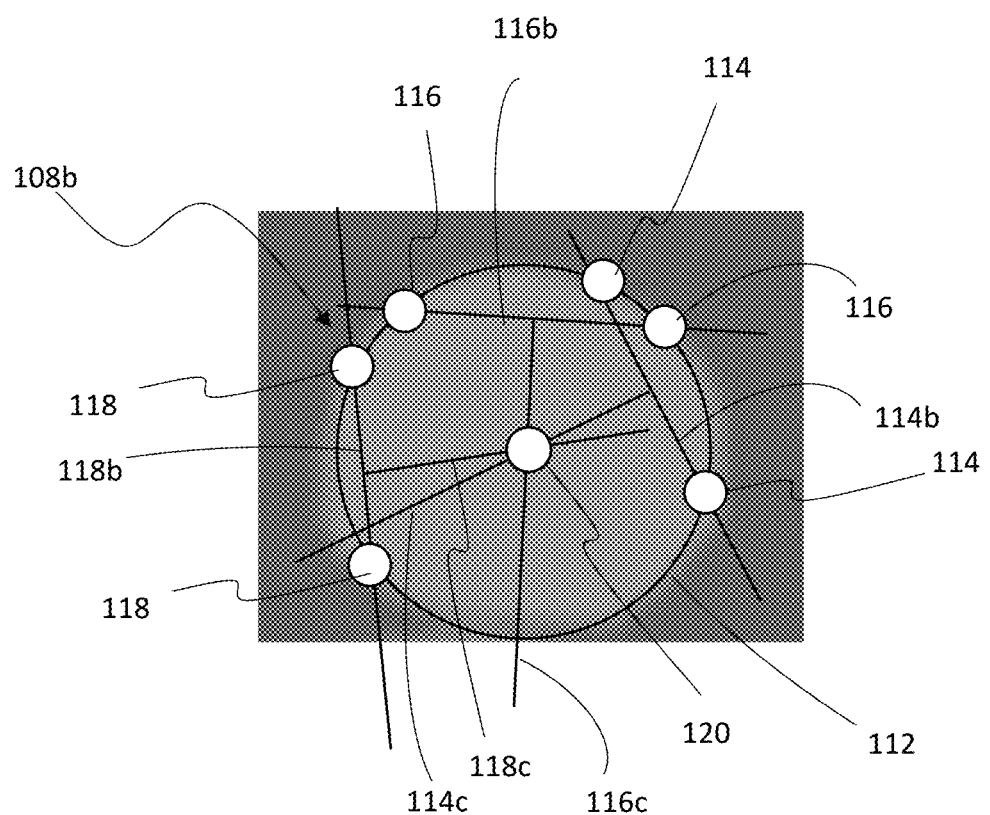
FIG. 8 is a diagram illustrating the steps performed in the flowchart of FIG. 7.
Figure 9:
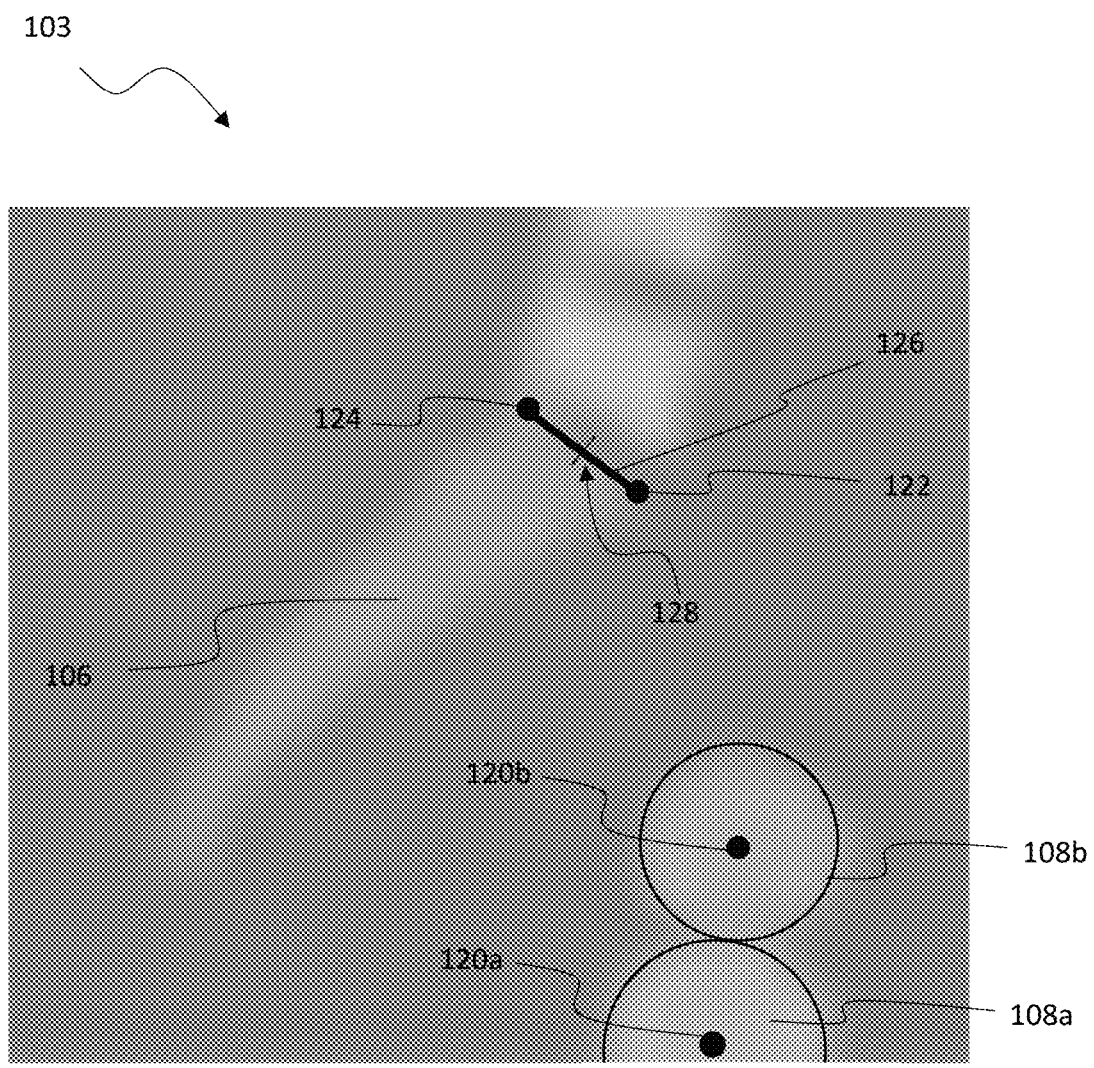
FIG. 9 is a closeup view of a representative image depicting anatomical landmarks.

In some embodiments, center of the femoral head or center of rotation of the femoral head is identified using a novel approach exemplified in FIGS. 7-9. This novel approach more accurately identifies the center of rotation of the femoral head than conventional approaches. Moreover, this approach is substantially more accurate than conventional approaches when a portion of the femoral head is damaged, abnormal, non-visible, or otherwise not visibly round. The process may be performed automatically using a trained computer system such as an ML machine or may include some amount of user assistance.

FIG. 7 provides a flowchart of an embodiment of the process in which the steps described are in reference to a single femoral head, but it should be understood that the process may be performed on each femoral head and may be performed on each femoral head simultaneously. First step 202 includes identifying the outer perimeter/boundary of the femoral head. Some embodiments further include creating digital circle 112 to represent the perimeter of the femoral head and then using perimeter circle 112 as the identified perimeter/boundary for the remainder of the steps.

Some embodiments identify the semi-circular perimeter of the opening of the acetabulum or create a digital representation of a semi-circular perimeter (or concentric circular perimeter) of the acetabulum. This approach may be necessary if the femoral head is too damaged, abnormal, or non-visible to identify an accurate perimeter of the femoral head.

Some embodiments may use both the femoral head and the acetabulum to establish an identifiable circular or semi-circular perimeter on which to perform the subsequent steps. This may also be necessitated by a patient having one healthy hip joint and one severely damaged or abnormal hip joint. For the remainder of the steps described in method 200, reference will be made to the perimeter of the femoral head, but this reference is interchangeable with the perimeter of the acetabulum.

Regardless of the perimeter identified in step 202, step 204 includes digitally inserting multiple pairs of points on the perimeter of the femoral head. FIG. 8 provides a closeup view of femoral head 108b with perimeter 112 and three pairs of perimeter points 114, 116, and 118. In some embodiments, only two pairs of perimeter points are used. Some embodiments use three pairs of perimeter points, and other embodiments use more than three pairs of points.

At step 206, lines 114b, 116b, and 118b are inserted between their respective points 114, 116, and 118. Then, at step 208, perpendicular lines 114c, 116c, and 118c are inserted from the respective midpoints of lines 114b, 116b, and 118b. Perpendicular lines 114c, 116c, and 118c extend radially inwardly relative to perimeter 112. Perpendicular lines 114c, 116c, and 118c may each intersect at the same point, which is identified as femoral head center point 120. However, in some instances perpendicular lines 114c, 116c, and 118c will not perfectly intersect at the same point. In such instances, the average of where all these lines intersect is identified as femoral head center point 120.

As exemplified in FIG. 9, some embodiments further include identifying the upper edge of the sacrum, i.e., the sacral plate. This process can be performed using known techniques. In some embodiments, the landmark points used to identify the sacral plate include anterior point 122 on the sacral top plate and posterior point 124 on the sacral top plate. The sacral plate top plate is then identified/highlighted by line 126 extending between the anterior and posterior points. Some embodiments further include identifying midpoint 128 of sacral top plate 126. As will be explained in subsequent paragraphs, sacral top plate line 126 and at least one center point of the femoral heads is used to measure spinopelvic measurements.

Figure 10:
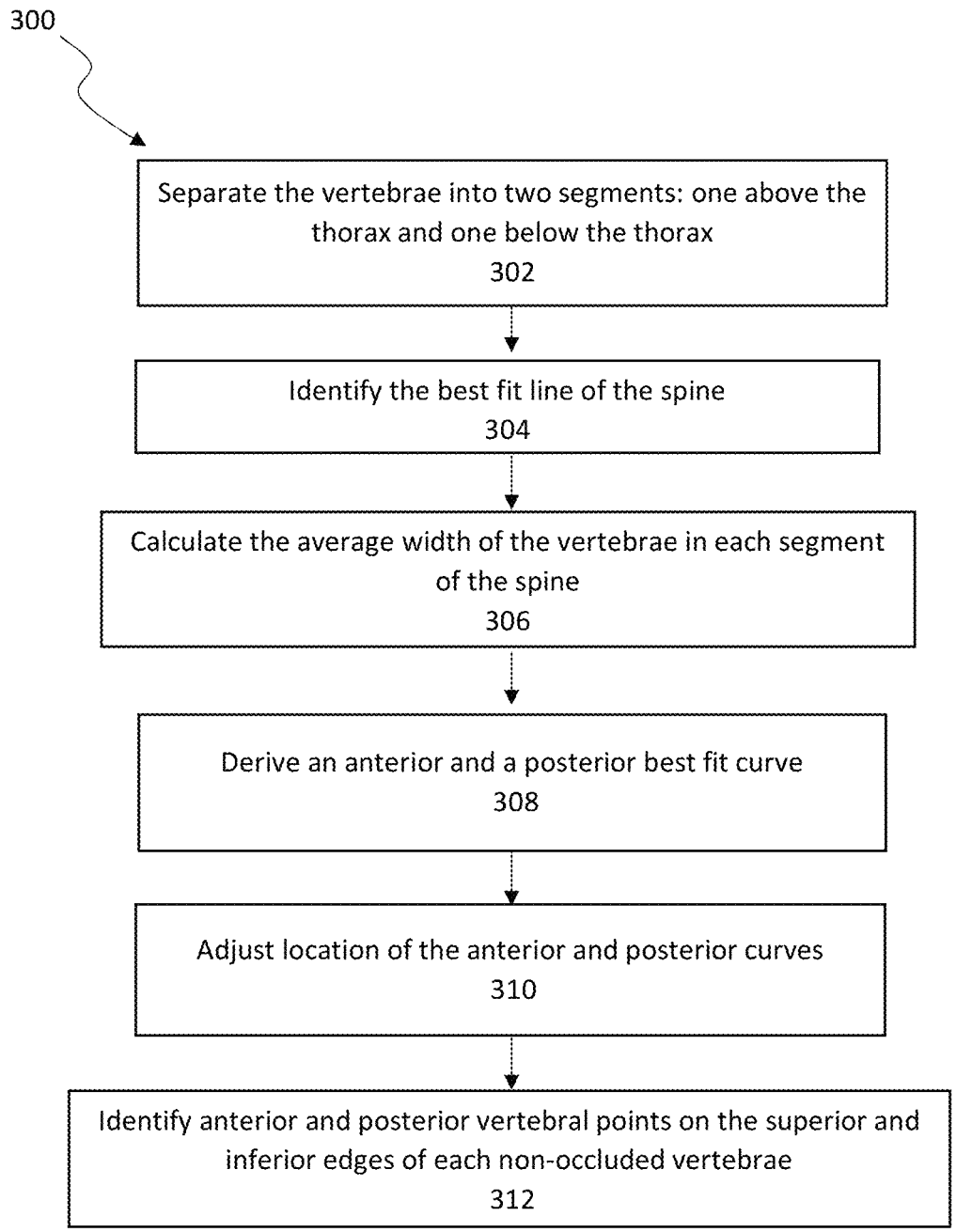
FIG. 10 is a is a flowchart an embodiment of one of the processes of the present invention.
Figure 11:
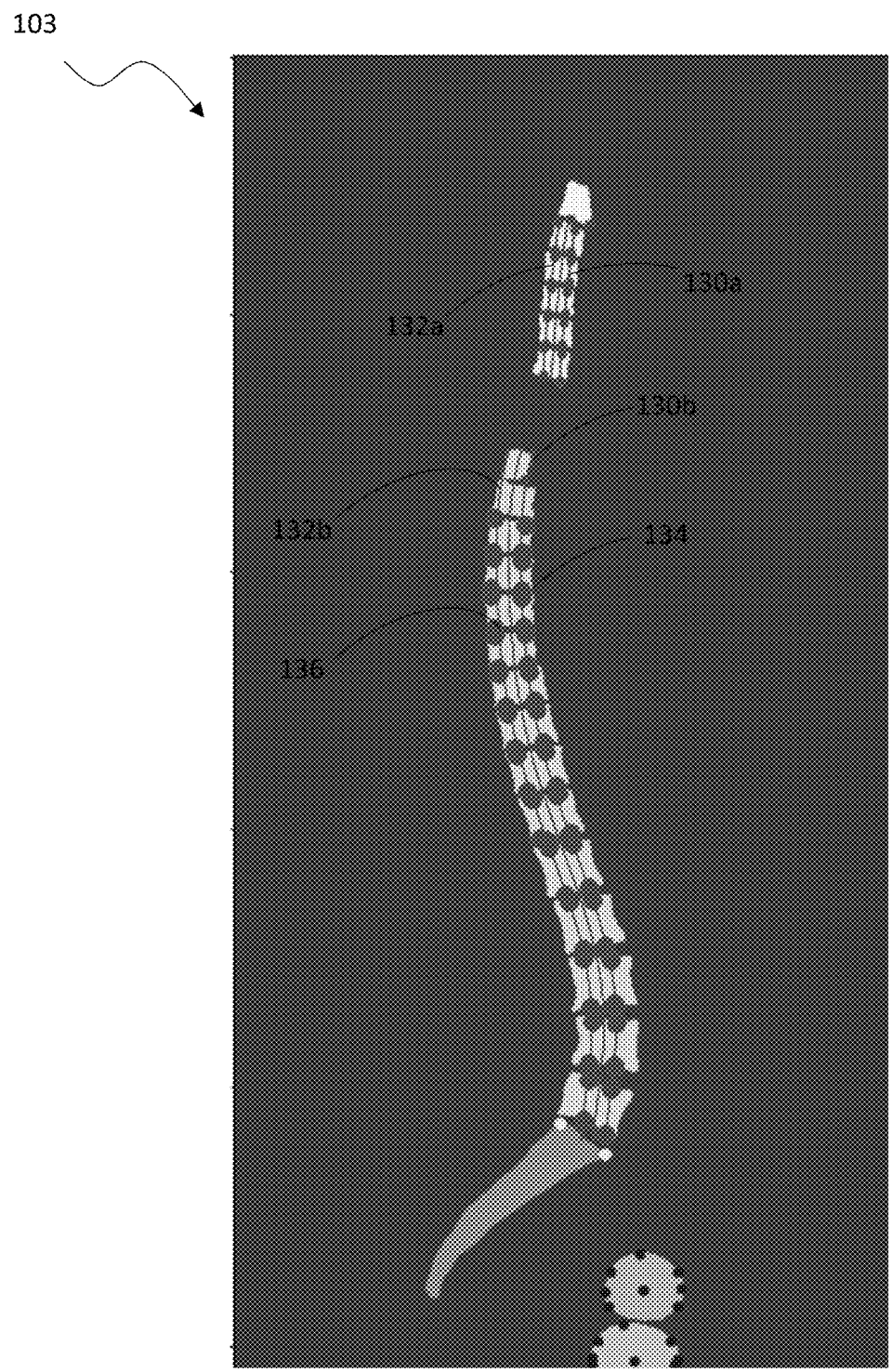
FIG. 11 is a modified representative image detailing the steps enumerated in the flowchart in FIG. 10.

Referring now to FIGS. 10-11, some embodiments further include identifying patient-specific spinal parameters using a plurality of spinal landmarks. As with the previously described processes, this process may be performed automatically using a trained computer system such as an ML machine or may include some amount of user assistance.

The patent-specific spinal parameters may include but are not limited to a spinal curvature line, average or minimum width (in an anterior to posterior direction, which is referred to herein as an "AP width") of the vertebrae one or sections of the spine (e.g., cervical, thoracic, and lumbar sections), average vertical spacing between the vertebrae in one or more sections of the spine, spinal inflection points, Cobb angles, lordosis/kyphosis angles, etc.

Spinal landmarks may include but are not limited to the inferior and superior edges (i.e., the upper and/or lower edges) of the cervical vertebrae, thoracic vertebrae and/or lumbar vertebrae. In some embodiments, the inferior and superior edges of each non-occluded vertebrae are identified using a pair of points on the superior edge and a pair of points on the inferior edge. The four of points on each vertebrae may be located at the four corners of said vertebrae.

Referring now to FIG. 10, some embodiments include the enumerated novel process for determining a patient's unique spinal curvature, which provides a better assessment of a person's anatomy for surgical considerations and can also be used to derive digital representations of occluded vertebrae. As explained previously, occluded vertebrae may prevent surgeons from capturing specific measurements that are crucial for a particular surgery.

With respect to identifying a patient's specific spinal curvature, conventionally, surgeons use the lordosis and kyphosis angle to assess spinal curvature. However, these values are typically measured using historic vertebrae landmarks such as the L1 vertebral edge and sacrum edge. These landmarks are used because they are easily reproducible for humans to measure on an image. However, doing this would not necessarily capture to full curvature of the hip and spine because it is ignoring the hip portion (i.e., portion inferior to the sacrum). Furthermore, one person's L1 might not be at the same place of curvature as another person's L1. Thus, using these historic landmarks fails to fully assess an individual's spinal curvature. In contrast, by finding the exact inflection points of the spine (including the sacrum) the present invention provides a more quantitative analysis of a patient's individual spinal morphology.

In some embodiment, the steps in FIG. 10 are performed for the entire spine. In some embodiments, the steps are performed for subsections of the spine (e.g., the cervical, thoracic, and lumbar sections). In some embodiments, the steps are performed on each section of the spine independently and then merged into a single spinal curvature line. In some embodiments, the spine is separated into vertebrae above the thorax and vertebrae below the thorax, e.g., step 302 in FIG. 10. For the sake of brevity, the description of the steps in FIG. 10 will be in reference to an embodiment in which the spine is separated into two sections, however the steps in FIG. 10 could be applied to more than two subdivisions of the spine or to the spine as a whole (at least the non-occluded vertebrae). With respect to depicted embodiments in FIGS. 10-11, the first section is above the thorax and the second section is below the thorax.

As exemplified in FIG. 10, step 304 includes identifying a best fit line for the curvature of the spine. In some embodiments determining the best fit line occurs by calculating the total pixel count of the spine and mathematically deriving the line that best fits the distribution of pixels.

As seen in the figures, the anterior-posterior width (hereinafter "AP width") of the vertebrae typically increase in moving in an inferior direction. Thus, some embodiments include step 306 for calculating the average vertebral AP width of the non-occluded vertebrae for each segment. In some embodiments, the average AP width is calculated based on the AP width of pixels of each vertebrae. In some embodiments, the average AP width is calculated based on the AP width of at least two or three vertebrae in each segment of the spine.

At step 308, for each segment, the calculated average AP width of the vertebrae is used to create anterior best fit curve 130 and posterior best fit curve 132 as shown in FIG. 11. The distance between anterior best fit curve 130 and posterior best fit curve 132 is equal to the calculated average AP width of the vertebrae for the segment. In some embodiments, the distance between anterior best fit curve 130 and posterior best fit curve 132 is equal to the vertebra with the smallest AP width in the segment.

In some embodiments, at step 310, anterior best fit curve 130 and posterior best fit curve 132 are moved in an anterior or a posterior direction to ensure that the two curves pass through each of the vertebrae in the segment. In some embodiments, the anterior best fit curve 130 and posterior best fit curve 132 are moved in an anterior or a posterior direction to ensure that the two curves pass through the majority of the vertebrae in the segment.

At step 312, anterior points 134 and posterior points 136 on both the superior and inferior edges are identified for each non-occluded vertebra in each segment. In some embodiments, the inferior and superior edges of at least 50% of vertebrae are identified in step 312. In some embodiments the inferior and superior edges of at least the vertebrae within the corresponding section of vertebrae are identified in step 312. The anterior and posterior points 134, 136 coincide with the edges of the vertebrae along anterior best fit curve 130 and posterior best fit curve 132, respectively.

In some embodiments, anterior points 134 and posterior points 136 are located along anterior and posterior lines 130, 132 where the pixels establish the edge of the vertebrae and the vertebral gaps. These intersections (or horizontal lines) are defined as the superior and inferior landmarks of each vertebrae.

Some embodiments start with a vertebral width ratio of 1, if these intersections are not filled up for many vertebrae (i.e., algorithm did not find a vertebral point), then the vertebral width ratio is decrease until as many possible marker points are identified on the spine. This step is performed for both the curves above and below the thoracic vertebrae to find as many possible points for the cervical, thoracic, and lumbar vertebrae.

As previously stated, some medical images will include occluded AOI. When the occluded AOI is one or more vertebrae, an embodiment of the present invention includes a novel process for identifying missing vertebrae and deriving representative vertebrae to fill in the gaps created by the occluded vertebrae. As previously explained, this approach may be performed automatically using a trained computer system such as an ML machine or may include some amount of user assistance.

Figure 12:
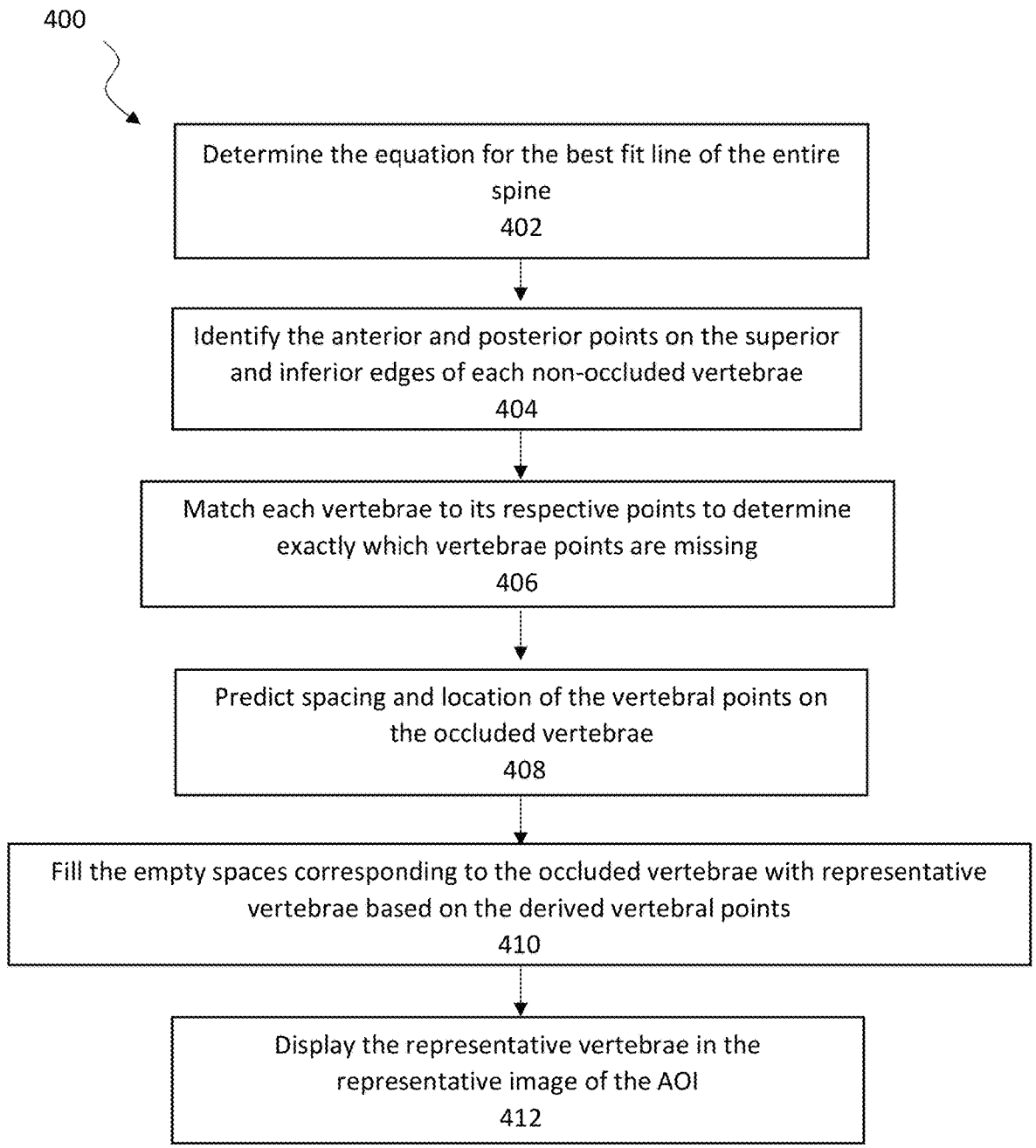
FIG. 12 is a flowchart an embodiment of one of the processes of the present invention.

As provided in FIG. 12, the novel process 400 for deriving occluded vertebrae includes step 402 for determining the individual polynomial equation of the entire spine (i.e., the best fit line representing the spinal curvature). At step 404, all the visible vertebral points are identified. At step 406, the system automatically matches each vertebrae to each of these points to determine exactly which vertebral points are missing. For example, given that a person generally has a set number of vertebrae, the system can start at one end of the spine and count vertebral points to determine which vertebra is missing.

Figure 13:
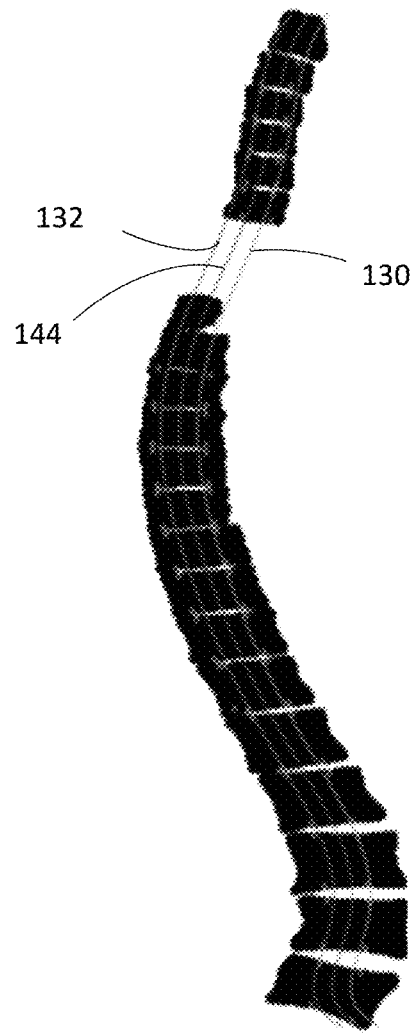
FIG. 13 is an exemplary representative figure illustrating the merging of the best fit lines for multiple segments of the patient's spine.
Figure 14:
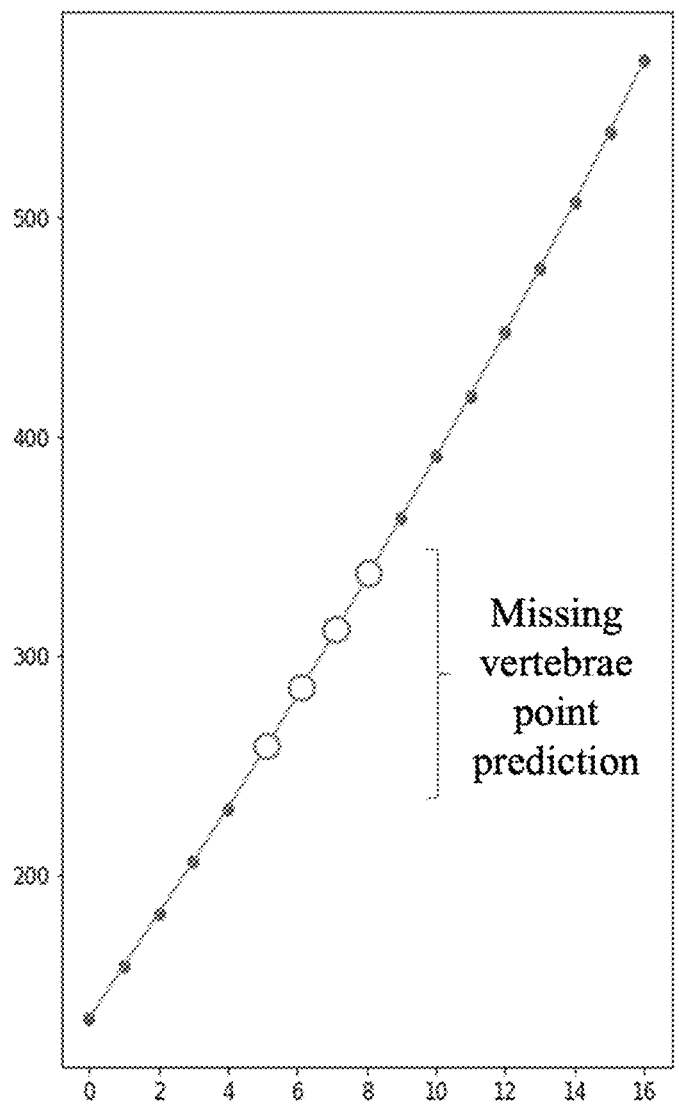
FIG. 14 is an exemplary plot predicting the location and spacing of the anterior vertebral points of the occluded vertebrae.
Figure 15:
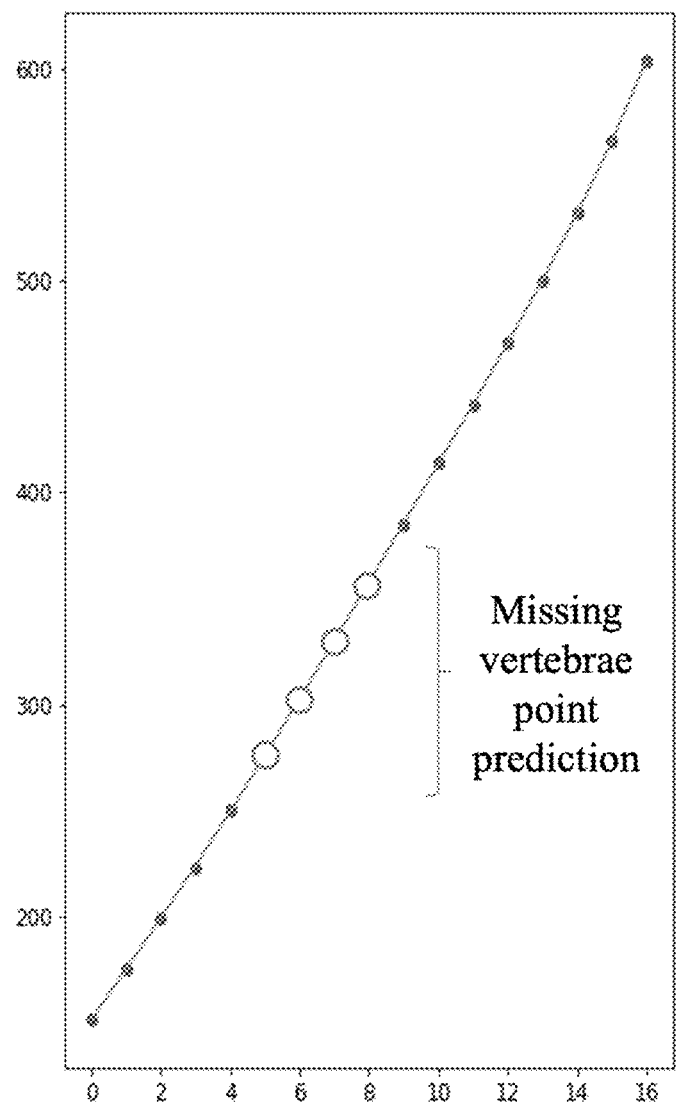
FIG. 15 is an exemplary plot predicting the location and spacing of the posterior vertebral points of the occluded vertebrae.

At step 408, some embodiments use anterior best fit line 130 for the anterior points to determine a mathematical relationship between the anterior points of each vertebrae (see e.g., FIG. 13). In doing so, the average vertical spacing between known anterior points can be calculated. Using the average vertical spacing and best fit curvature line 130, anterior points can be derived for the occluded vertebrae. The same steps are also performed for the posterior vertebral points. Some embodiments include plotting the missing and existing pixel values of the vertebral points to create a polynomial relationship as exemplified in FIGS. 14 and 15.

Figure 16:
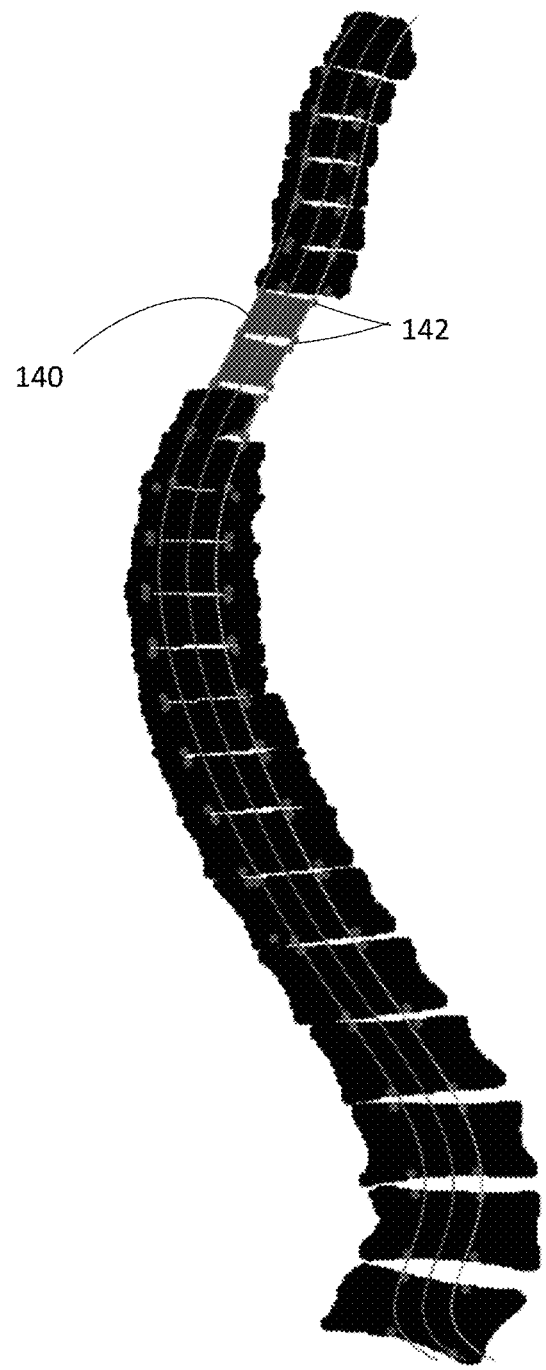
FIG. 16 is an exemplary image depicting the digital insertion of representative vertebrae for the occluded vertebrae.
Figure 17:
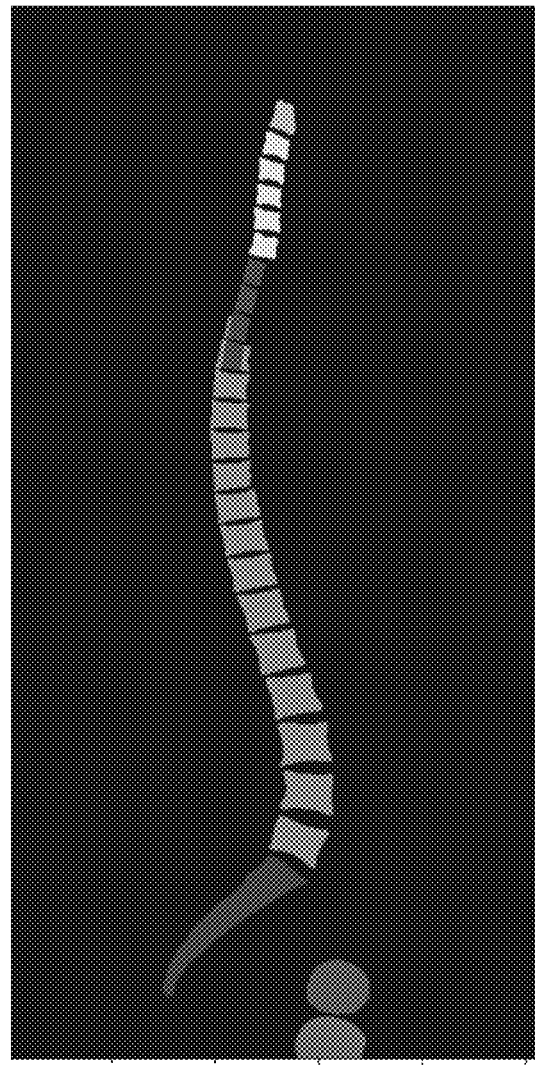
FIG. 17 is a modified segmentation image with the representative vertebrae for the occluded vertebrae digitally inserted into their predicted locations on the spine.

In some embodiments, at step 410 the empty spaces corresponding to the occluded vertebrae are filled with representative vertebrae 140 based on the derived vertebral points 142 corresponding to the missing/occluded vertebrae as depicted in FIG. 16. In some embodiments, at step 412, the points are plotted back on representative image 103 as depicted in FIG. 17 to fill in the occluded vertebral points.

Figure 18:
FIG. 18 is a display of various spinal and pelvic landmarks and measurements digitally inserted onto the medical image.

At this point, the hip and spine landmarks have been identified. For example, the hip landmarks may include the center of the femoral head(s) and the sacral end plate. Using these landmarks, the present invention can calculate hip parameters by connecting the landmarks together via lines and measuring the angles between these lines as exemplified in FIG. 18. For example, pelvic tilt, sacral slope, and pelvic incidence can all be calculated in accordance with FIG. 1. It should be understood that additional hip landmarks can be identified, and additional hip parameters can be calculated.

Figure 19:
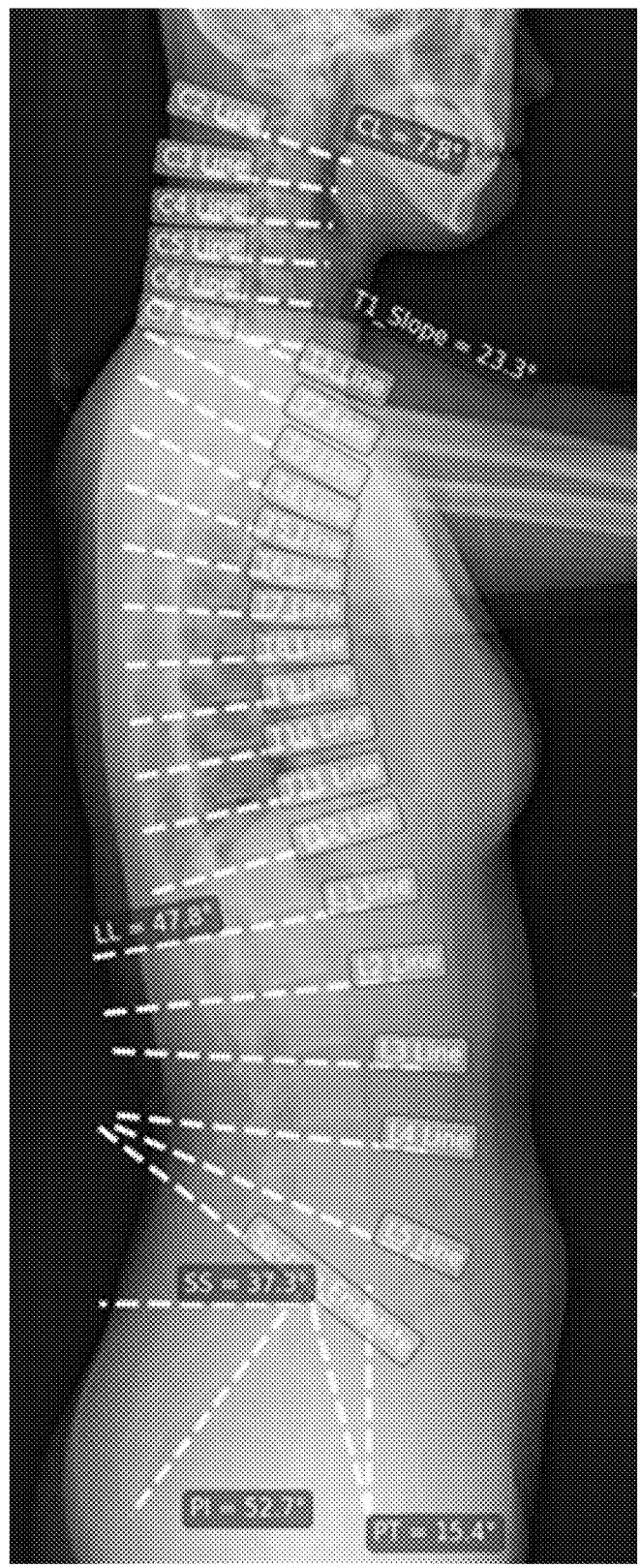
FIG. 19 is a display of various spinal and pelvic measurements digitally inserted onto the medical image.

With respect to the spine, including occluded AOI in some embodiments, non-limiting landmarks include vertebral body corner points and the sacral end plate. Using these landmarks and/or other anatomical landmarks, the present invention can calculate and display various spinal parameters as depicted in FIG. 19 by measuring the angles between these relevant points. These spinal parameters include but not limited to all possible Cobb angles, lordosis/kyphosis angles, etc.

Figure 20:
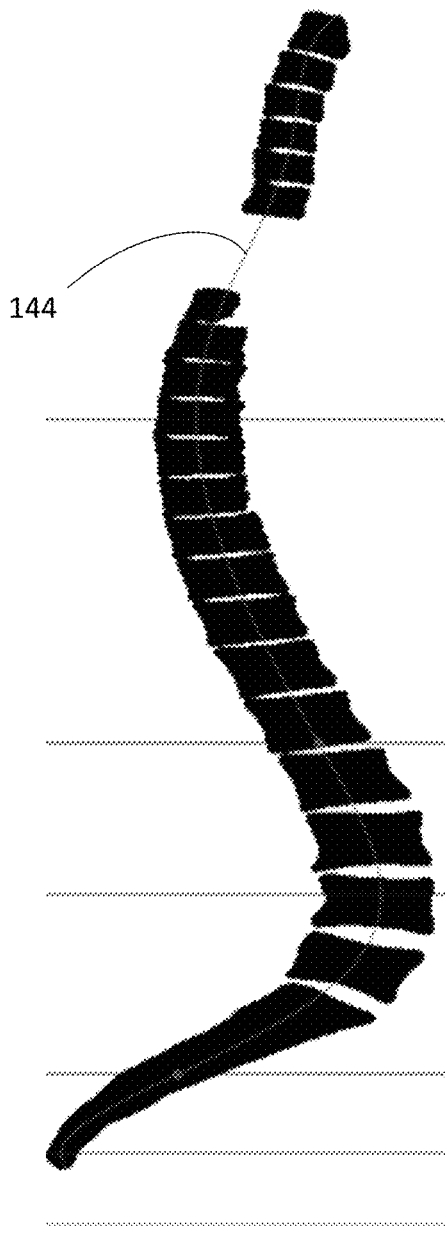
FIG. 20 is an exemplary display of the best fit line for the curvature of the spine and sacrum.

As previously explained, patient-specific spinal inflection points provide a more quantitative analysis of a patient's individual spinal morphology. Thus, some embodiments of the present invention determine a patient's individual spinal morphology by finding the line of best fit 144 for the combination of the spine and sacrum as exemplified in FIG. 20. In some embodiments, best fit line 144 extends through the entire spine and sacrum based on entire pixel distribution of vertebral pixels.

Figure 21:
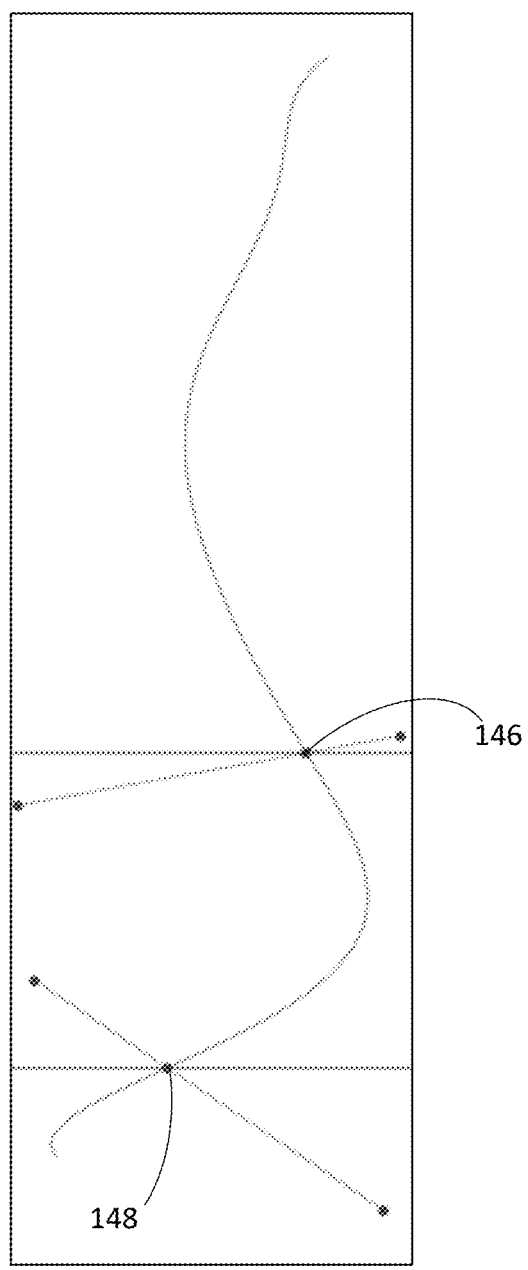
FIG. 21 is an exemplary plot of the inflection points for the curvature of the spine and sacrum.

From the spinal polynomial equation, the present invention uses the mathematical derivative of the equation to find exactly at which vertebrae or spinal points 146, 148 that the spinal curvature changes as exemplified in FIG. 21. These points establish the patient-specific kyphosis and lordosis curvature of a patient's spine. These points define essentially how curved a patient's back is. This is important for a patient's sagittal balance, which affects patient's motion after a total hip arthroplasty and has impacts on dislocation risk.

Traditionally, hip-spine parameters are measured to determine optimal acetabular cup component selection for patients undergoing total hip arthroplasty. This largely depends on the lumbar lordosis, which as stated is currently measured at historic landmarks and may not be patient curvature specific. The inflection points derived from this analysis assess the patient curvature more individually and this new value (i.e., modified lumbar lordosis) is used for optimal prosthesis selection.

By calculating the various patient-specific parameters above, a surgeon can better determine surgical plan, select more appropriate prothesis, and more precisely execute a patient-specific surgery.

Hardware and Software Infrastructure Examples

The present invention may be embodied on various computing systems and/or platforms that perform actions responsive to software-based instructions. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++, Visual Basic or the like and conventional procedural programming languages, such as the "C" programming language or similar programming languages.

Aspects of the present invention may be described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method for determining patient-specific anatomical parameters, comprising:
    acquiring medical images of a patient;
    identifying anatomy of interest in the acquired medical image, wherein the anatomy of interest includes at least a portion of a spine, at least one femoral head, and at least a portion of a sacrum;
    segmenting the anatomy of interest to create a digital representative image of the anatomy of interest separate from the acquired medical image;
    identifying a series of anatomical landmarks on the anatomy of interest, wherein the anatomical landmarks include at least one parameter from a group comprising a center point of the at least one femoral head, a sacral end plate, and anterior and posterior vertebral points on a superior and inferior edge of one or more vertebrae;
    in response to a determination that the anatomy of interest includes occluded vertebrae:
        calculating a best fit line of a curvature of the spine;
        calculating an average anterior-posterior (AP) width of at least some vertebrae;
        calculating an anterior best fit line and a posterior best fit line, wherein the anterior best fit line is spaced from the posterior best fit line a distance generally equal to or less than the calculated average AP width;
        identifying an anterior point and a posterior point on both the superior edge and the inferior edge of the at least some vertebrae;
        calculating a location of the occluded vertebrae with respect to an immediately adjacent vertebrae based on a spacing between the anterior points and the posterior points of the immediately adjacent vertebrae;
        digitally inserting a digital representation of the occluded vertebrae into the representative image;
    quantitatively determining patient-specific spinal inflection points based on the best fit line of the curvature of the spine;
    quantitatively determining patient-specific spinopelvic parameters based on at least the center point of the at least one femoral head, a sacral slop, and the patient-specific inflection points of the spine; and displaying on a graphic user interface the patient-specific spinopelvic parameters.

2. The method of claim 1, wherein identifying the center point of the at least one femoral head includes:
placing two or more pairs of points along a perimeter boundary of the at least one femoral head;
identifying a midpoint between a line extending between each pair of points;
extending a perpendicular line from each midpoint and identifying a point of intersection or an average point of intersection amongst the perpendicular lines; and
identifying the point of intersection or the average point of intersection as the center point.

3. The method of claim 1, wherein the spinopelvic parameters include a pelvic tilt, a pelvic incidence, a sacral slope angle, one or more Cobb angles, a lordosis angle, and a kyphosis angle.

4. The method of claim 1, wherein determining the spinal inflection points is based on calculating a derivative of an equation representing the best fit line of the curvature of the spine.

5. The method of claim 1, further including separating the spine into two or more segments in response to the anatomy of interest including occluded vertebrae.

6. A method for determining patient-specific anatomical parameters, comprising:
acquiring digital medical images of a patient;
identifying anatomy of interest in the acquired medical image, wherein the anatomy of interest includes at least a portion of a spine;
segmenting the anatomy of interest to create a digital representative image of the anatomy of interest separate from the acquired medical image;
identifying a series of anatomical landmarks on the anatomy of interest, wherein the anatomical landmarks include at least an anterior or posterior vertebral point on a superior and inferior edge of one or more vertebrae;
in response to a determination that the anatomy of interest includes occluded vertebrae:
calculating a best fit line of a curvature of the spine;
calculating an average anterior-posterior (AP) width of at least some vertebrae;
calculating an anterior best fit line and a posterior best fit line, wherein the anterior best fit line is spaced from the posterior best fit line a distance generally equal to or less than the calculated average AP width;
identifying an anterior point and a posterior point on both the superior edge and the inferior edge of the at least some vertebrae;
calculating a location of the occluded vertebrae with respect to an immediately adjacent vertebrae based on a spacing between the anterior points and the posterior points of the immediately adjacent vertebrae;
digitally inserting a digital representation of the occluded vertebrae into the representative image;
quantitatively determining patient-specific spinal inflection points based on the best fit line of the curvature of the spine;
displaying on a graphic user interface the patient-specific spinal inflection points.

7. The method of claim 6, further including separating the spine into two or more segments in response to the anatomy of interest including occluded vertebrae.

8. The method of claim 6, wherein the anatomy of interest further includes at least one femoral head, or at least a portion of a sacrum.

9. The method of claim 8, further including identifying a center point of the at least one femoral head.

10. The method of claim 9, wherein identifying the center point of the at least one femoral head includes:
placing two or more pairs of points along a perimeter boundary of the at least one femoral head;
identifying a midpoint between a line extending between each pair of points;
extending a perpendicular line from each midpoint and identifying a point of intersection or an average point of intersection amongst the perpendicular lines; and
identifying the point of intersection or the average point of intersection as the center point.

11. The method of claim 9, further including:
quantitatively determining patient-specific spinopelvic parameters based on at least the center point of the at least one femoral head, a sacral slop, and the patient-specific inflection points of the spine; and
displaying on a graphic user interface the patient-specific spinopelvic parameters.

12. The method of claim 11, wherein the spinopelvic parameters include a pelvic tilt, a pelvic incidence, a sacral slope angle, one or more Cobb angles, a lordosis angle, and a kyphosis angle.

13. The method of claim 6, wherein determining the spinal inflection points is based on calculating a derivative of an equation representing the best fit line of the curvature of the spine.

14. The method of claim 8, wherein the series of anatomical landmarks on the anatomy of interest further include a center point of the at least one femoral head and a sacral end plate.

15. A method for determining patient-specific anatomical parameters, comprising:
acquiring medical images of a patient;
identifying anatomy of interest in the acquired medical image, wherein the anatomy of interest includes at least a portion of a spine, at least one femoral head, and at least a portion of a sacrum;
segmenting the anatomy of interest to create a digital representative image of the anatomy of interest separate from the acquired medical image;
identifying a series of anatomical landmarks on the anatomy of interest, wherein the anatomical landmarks include at least one parameter from a group comprising a center point of the at least one femoral head, a sacral end plate, and anterior and posterior vertebral points on a superior and inferior edge of one or more vertebrae;
calculating a best fit line of a curvature of the spine;
quantitatively determining patient-specific spinal inflection points based on the best fit line of the curvature of the spine;
quantitatively determining patient-specific spinopelvic parameters based on at least the center point of the at least one femoral head, a sacral slop, and the patient-specific inflection points of the spine; and
displaying on a graphic user interface the patient-specific spinopelvic parameters.

16. The method of claim 15, wherein identifying the center point of the at least one femoral head includes:
placing two or more pairs of points along a perimeter boundary of the at least one femoral head;
identifying a midpoint between a line extending between each pair of points;

extending a perpendicular line from each midpoint and identifying a point of intersection or an average point of intersection amongst the perpendicular lines; and identifying the point of intersection or the average point of intersection as the center point.

17. The method of claim 15, wherein the spinopelvic parameters include a pelvic tilt, a pelvic incidence, a sacral slope angle, one or more Cobb angles, a lordosis angle, and a kyphosis angle.

18. The method of claim 15, wherein determining the spinal inflection points is based on calculating a derivative of an equation representing the best fit line of the curvature of the spine.

19. The method of claim 15, further including separating the spine into two or more segments in response to the anatomy of interest including occluded vertebrae.

20. The method of claim 15, further including in response to a determination that the anatomy of interest includes occluded vertebrae:

calculating an average anterior-posterior (AP) width of at least some vertebrae;

calculating an anterior best fit line and a posterior best fit line, wherein the anterior best fit line is spaced from the posterior best fit line a distance generally equal to or less than the calculated average AP width;

identifying an anterior point and a posterior point on both the superior edge and the inferior edge of the at least some vertebrae;

calculating a location of the occluded vertebrae with respect to an immediately adjacent vertebrae based on a spacing between the anterior points and the posterior points of the immediately adjacent vertebrae; and digitally inserting a digital representation of the occluded vertebrae into the representative image.

\* \* \* \* \*